United States Patent [19]
Patat et al.

[11] Patent Number: 5,985,315
[45] Date of Patent: Nov. 16, 1999

[54] METHOD OF PREPARING A BIOLOGICAL GLUE ABLE TO COAGULATE SIMPLY BY ADDITION OF CALCIUM IONS

[75] Inventors: Jean-Louis Patat, Paris; Olivier Delmas, Montbazon; Roland Schmitthaeusler, Motigny le Bretonneux, all of France

[73] Assignee: Inoteb, Saint-Gonnery, France

[21] Appl. No.: 09/001,223

[22] Filed: Dec. 30, 1997

[30] Foreign Application Priority Data

Dec. 30, 1996 [FR] France ..................... 96 16214

[51] Int. Cl.$^6$ ..................... A61L 15/16
[52] U.S. Cl. ................. 424/443; 424/444; 424/455
[58] Field of Search ................. 424/443, 444, 424/455

[56] References Cited

FOREIGN PATENT DOCUMENTS 10-592242  4/1994  European Pat. Off. .
57-050923  3/1982  Japan .
WO 93-19805  10/1993  WIPO .

*Primary Examiner*—Jose' G. Dees
*Assistant Examiner*—Kathryne E. Shelborne
*Attorney, Agent, or Firm*—Oliff & Berridge, PLC

[57] ABSTRACT

By placing a blood plasma in contact with a blood coagulation contact phase activator, before or during preparation of a fibrinogen-based biological glue, a preactivated biological glue is obtained which does not coagulate spontaneously but which is capable of coagulating in less than 5 minutes simply by the addition of calcium ions, without the addition of thrombin. The process has application to the field of surgery.

29 Claims, 1 Drawing Sheet

METHOD OF PREPARING A BIOLOGICAL GLUE ABLE TO COAGULATE SIMPLY BY ADDITION OF CALCIUM IONS

BACKGROUND OF THE INVENTION

The invention relates to a method for preparing a biological glue capable of coagulating simply by addition of calcium ions.

It is known that protein concentrates containing fibrinogen and factor XIII in particular can coagulate by adding thrombin to produce a fibrin network, and are used as adhesives. More specifically, under the effect of the thrombin, the fibrinogen is converted into fibrin monomer. The fibrin monomers assemble into fibrin polymers. Under the action of factor XIII activated by thrombin, in the presence of calcium ions, the fibrin chains are crosslinked. Thus, the addition of thrombin, followed by application of the resulting mixture, causes coagulation by formation of fibrin on the parts to be glued, by a mechanism that mimics the end phase of blood coagulation. Thus, by coagulating, the fibrinogen concentrates constitute a glue that can join living tissue and keep it joined while producing a hemostatic action; see for example patent FR-2448900. Such glues are commonly called "biological glues" or "fibrin glues" and are used in surgery, particular to prevent or stop bleeding, replace or reinforce suture threads, hold grafts in place, for example skin grafts, bring together tissues that have undergone resection, for example in lung or gastrointestinal tract surgery, or to glue parts of prostheses, etc.

When biological glues are used, thrombin should be available, prepared from human or animal blood plasma mixtures. Homologous products, i.e. products of human origin for which the donor and recipient are different, carry the risk of contaminating the recipient by pathogens from the donor. This risk can be reduced by donor selection and screening for pathogen markers in the donor, or physical/chemical treatments that destroy the prepared products or diminish their virulence. However, there can be no certainty that homologous products are safe.

Products prepared from animal tissues also carry risks linked to the existence of pathogens transmissible to humans, and also risks of immunization and hence anaphylactic reactions.

The above risks would be avoided if solely autologous products, i.e. products prepared only from material taken from the future recipient, were used.

The principle of autologous transfusion is known and extremely widespread, as is the preparation of fibrinogen-based glues. However, the so-called "autologous" glues are only truly autologous as far as the fibrinogen solution is concerned. In fact, the thrombin solution is obtained from homologous or heterologous plasmas, but not autologously; see in particular Cederholm-Williams, *Lancet* 344, 336–337 (1994).

Patent Application PCT WO94/07548 describes a biological glue enriched with platelet factors that is able to coagulate without addition of thrombin by adding, to the recalcified glue, an activator of the blood coagulation contact phase such as kaolin. However, in this patent application, the contact phase activator is incorporated at the time the glue is used, which makes activation uncertain and difficult because the fibrinogen concentrate is a highly viscous product, difficult to handle. As a result, coagulation time is difficult to control. Moreover, since coagulation progresses along with activation, it is difficult to separate the activator from the activated glue.

SUMMARY OF THE INVENTION

It has now been discovered that it is possible to obtain a biological glue coagulable simply by addition of calcium ions, without adding a contact phase activator at the time the glue is used, and without adding thrombin or prothrombin before use or at the time of use. It has been discovered that it is possible to preactivate the plasma used for preparing the biological glue before obtaining the fibrinogen concentrate containing coagulation factors, and without coagulation being observed during preparation of the glue.

In particular, it has been discovered that one need only preactivate the plasma with a coagulation contact phase activator for a sufficient time to partially activate the prekallikrein into kallikrein, and that a biological glue capable of coagulating relatively rapidly, simply by recalcification, without adding thrombin, can then be obtained from the plasma thus treated, without spontaneous coagulation.

U.S. Pat. No. 4,427,650 describes a fibrin glue in the form of a powder containing a mixture of fibrinogen and thrombin and/or prothrombin. A glue of this type undergoes no activation and hence contains no activated coagulation factors not dependent on calcium ions.

Document WO91/09641 describes a fibrin glue containing fibrinogen and added thrombin. This glue is prepared in such a way that the thrombin activity is inhibited. According to one particular embodiment, this glue has no calcium ions, as these are not added until the time of use. However, such a glue, which contains added thrombin, coagulates spontaneously even without the addition of calcium ions, after about 90 seconds. When calcium ions are added, it coagulates in less than 2 seconds. In other embodiments, coagulation of the glue is slowed down by acidifying it to a pH of less than 5.5, which inhibits thrombin activity, and means of increasing the pH are used at the time of use to nullify the inhibition effect. According to another embodiment, a photosensitive thrombin inhibitor deactivated by light is added to the glue in a dark place. Such a glue, whatever its embodiment, contains no activated coagulation factors not dependent on calcium ions.

The glue obtained according to the invention is, on the contrary, a stable glue which, in the form of an aqueous solution, does not coagulate spontaneously at room temperature, even in the light, and is able to coagulate merely by addition of calcium ions, without changing the pH. It contains activated coagulation factors that do not depend on calcium ions.

The biological glue obtained according to the invention is a preactivated glue containing fibrinogen and at least one activated coagulation factor whose activation does not depend on calcium ions. It is stable in aqueous solution, i.e. the solution does not coagulate spontaneously, for at least one hour at a temperature of 20° C., and is able to coagulate in less than 5 minutes simply by addition of calcium ions, without being contacted by an activator.

Thus, the biological glue obtained according to the invention is able to coagulate without the addition of thrombin or prothrombin.

This glue can be in the form of an aqueous solution. It can also be in the form of a lyophilizate from which an aqueous solution can be reconstituted at the time of use.

The mechanisms of blood coagulation are essentially known. It is known that one of the initial coagulation activation mechanisms can easily be reproduced in vitro by having the plasma contact an activator, which can be an insoluble solid with a negatively charged surface, such as glass or kaolin, or a soluble activator, in the dissolved state. This initial activation results from the interaction between several plasma proteins: factor XII, factor XI, prekallikrein, and high-molecular-weight kininogen (HMWK); see for example Wachtfogel et al., *Thrombosis Research,* 72, 1–21 (1993). On contact with the activating surface, the spatial configuration of factor XII undergoes a change. The factor XII then becomes capable of activating the prekallikrein into kallikrein, and this reaction is amplified by HMWK. The kallikrein thus formed acts on the factor XII and converts it into activated factor XII (or factor XIIa). Factor XIIa has the property of activating factor XI.

These reactions involving factor XII, prekallikrein, HMWK, and factor XI are called "contact system reactions," and the coagulation factors involved are called "contact system factors" or "contact factors."

The coagulation phase during which the contact system reactions occur is called the "contact phase."

The mechanisms leading to coagulation also involve: activation of factor IX by factor XIa, a process that requires the presence of calcium ions; activation of factor X under the action of a complex formed by factors IXa, VIIIa, and PF3 (platelet factor 3), in the presence of calcium ions; and activation of prothrombin into thrombin under the influence of a complex of factors Xa, Va, and PF3, in the presence of calcium ions. The thrombin can convert fibrinogen into so-called "soluble" fibrin and, in the presence of calcium ions, can also activate factor XIII. Activated factor XIII can convert soluble fibrin into insoluble fibrin which forms the blood clot.

It is known that another coagulation pathway, called the extrinsic pathway, involves activation of factor VII under the action of tissue thromboplastin. The activated factor VII is able to activate factor X, and also factor IX. Also, it is known that activated factor XII is able to activate factor VII. Thus, activation of factor VII can result from activation of the contact phase.

The invention is based in particular on the discovery of the fact that, by partially activating the contact system factors, for example on the starting plasma, and in any event before obtaining the fibrinogen concentrate of which the glue is composed, one can eventually obtain a biological glue able to coagulate rapidly simply by the addition of calcium ions, without the addition of either thrombin or prothrombin. It has been found that such partial activation effected at an early stage does not bring about spontaneous premature coagulation during the operations involved in obtaining the fibrinogen concentrate of which the biological glue is made. More specifically, it has been found that one need only place the plasma in contact with the activator in a sufficient quantity and for a sufficient time for the plasma to contain at least 15, and in particular at least 20, kallikrein units per liter. The biological glue obtained with such a preactivated plasma is then able to coagulate in less than 5 minutes, without the addition of an activator and without the addition of thrombin or prothrombin, merely by recalcification.

The kallikrein unit used here is defined as follows: it is the quantity able to hydrolyze a 0.52 mM solution of D-prolyl-L-phenylalanyl-L-arginine-p-nitroanilide in a veronal-sodium acetate buffer solution with a pH of 7.35, at 37° C., at the initial rate of 1 $\mu$mol/min.

The biological glue obtained according to the invention is characterized in particular by containing at least one activated coagulation factor whose activation does not depend on calcium ions, chosen from factor XIIa, factor XIa, factor VIIa, and kallikrein. These activated factors can be detected and/or assayed for example by the following methods:

Factor XIIa (also known as "prekallikrein activator"): European Pharmacopeia, 1994, Chapter V.2.1.11;

Factor VIIa: method of Morrissey et al., *Blood,* Vol. 81, pp. 734–744 (1993); the Staclot VIIa-rTF commercial kit from Diagnostic Stago, no. 00281, can be used in particular;

Factor XIa: chronometric method of Gyöngyössi-Issa Mic et al., *Vox Sang.*, Vol. 70, pp. 76–85 (1996); or chromogenic method of C. F. Scott and R. W. Colman, *Proc. Natl. Acad. Sci. USA*, Vol. 89, pp. 11189–11193 (1992);

Kallikrein: see experimental part below.

The stability of the biological glue obtained according to the invention, attested by the absence of spontaneous coagulation at room temperature, shows that it is practically thrombin-free. The biological glue obtained according to the invention is also practically fibrin-free, as attested by its low fibrinopeptide A content (in general, after the method according to the invention, less than 0.5 wt. % of the fibrinogen present in the starting plasma has been split with formation of fibrinopeptide A; see experimental part below). On the other hand, this biological glue contains coagulation factors in the nonactivated form whose activation depends on calcium ions. It thus contains in particular, in addition to prothrombin, factors XIII, X, V, and PF3. In general, it also contains factors VIII and IX, which are necessary for coagulation in the absence of activated factor VII.

Hence the invention relates to a method for preparing a biological glue as defined above. It is a method comprising the steps of: a) obtaining blood plasma containing an agent capable of complexing calcium ions, b) obtaining from said plasma a biological glue based on fibrinogen and coagulation factors, and c), if desired, subjecting the biological glue obtained to freeze-drying, wherein, before or during step b), said plasma is placed in contact with a contact phase activator. The biological glue may be obtained from the plasma by known methods.

Of course, the conditions (quantity and duration of activator application) that yield a concentration of at least 15 kallikrein units, or more simply, that yield a biological glue according to the invention, namely one able to coagulate in less than 5 minutes simply by the addition of calcium ions, can be determined once and for all. Thus it is unnecessary to assay the kallikrein each time the method is followed.

The step in which the plasma is made to contact the activator is preferably carried out at a temperature of less than 10° C. For example, one operates at a temperature of 1 to 8° C. and in particular at approximately 4° C.

When the activator is insoluble, one may if desired separate the preactivated plasma from the activator. For this purpose, after a sufficient contact time, the activator is separated and eliminated, for example by filtration. The contact time sufficient for achieving at least partial conversion of prekallikrein into kallikrein obviously depends on the nature of the activator, and the quantity of activator. This time can be determined in each case by simple routine experiments; see for example the experimental part below.

The agents capable of complexing the calcium ions are known. These are for example citric acid salts such as sodium citrate, or a chelating agent such as an EDTA salt (for example an EDTA sodium salt).

The starting plasma can also contain a soluble zinc salt such as sulfate or acetate in order to obtain for example a zinc ion concentration of approximately $10^{-4}$ M to $10^{-2}$ M. It is known that zinc ions act as contact system reaction accelerators.

In the case of an insoluble solid activator, the contact between the plasma and the activator can be brought about in an appropriate container. The activator is introduced into the container before or after the plasma is introduced. The activator can be made to adhere to the inside wall of the container. For example, the inside wall can be coated with activator. When the activator does not adhere to the inside wall of the container, a step should be provided in which, after a sufficient contact time, the activator and the activated plasma are separated. For this purpose, for example, the container can be provided on the inside or the outside with a filter that allows the plasma to pass through and holds back the activator in order to separate the activated plasma from the activator after the contact step.

According to another embodiment, this contacting process is carried out by circulating said plasma in a column containing the activator. For example, said plasma can be circulated in the column up to an outlet orifice, said outlet orifice being provided with a filter that holds back the activator. After a sufficient contact time, the activated plasma is then collected, while the filter holds back the activator.

When production of biological glue includes a step consisting of concentrating the plasma, for example with the aid of a membrane allowing water and low-molecular-weight components to pass through but holding back the proteins, the plasma can be placed in contact with the activator during this concentration step. If the activator is an insoluble solid, it must then be separated, for example by filtration, from the concentrated or partially concentrated plasma.

The coagulation contact phase activators are well known. They are in particular solids whose surfaces are negatively charged, such as glass, kaolin, Celite, zinc oxide, zinc carbonate, etc.

Soluble activators such as dextran sulfate and ellagic acid can also be used.

It has also been found that other products such as calcium carbonate (aragonite or calcite) are able to activate the contact system. Thus, an activator made essentially of aragonite, for example in the form of coral particles, can be used. For example, particles with a particle size of 0.3 to 2 mm can be used.

It has been found that activation by calcium carbonate increases the plasma calcium concentration slightly, but not enough to trigger premature coagulation when the biological glue is prepared.

Soluble activators immobilized on solid substrates by traditional techniques such as covalence or affinity can also be used. Such substrates on which soluble activators are immobilized are equated with the insoluble activators and are used like them.

The activators used in the method according to the invention should not retain a noteworthy proportion of (in the case of a solid activator), nor inhibit, the coagulation factors whose activation depends on calcium ions and which are necessary to the sequence of reactions leading to fibrin formation and fibrin coagulation. The factors necessary for this reaction sequence are essentially, in addition to prothrombin, factors V, VIII, IX, X, PF3, and XIII.

In fact, appropriate activators can easily be selected by routine experiments: an activator is appropriate if it leads to a biological glue according to the definition given above, namely a stable biological glue coagulating in less than 5 minutes simply by the addition of calcium ions.

It has been found that preactivation of the coagulation contact phase does little to activate the platelets: less than 10% of the platelets are activated. Hence, either a plasma containing no platelets or few platelets, or a platelet-containing or a platelet-rich plasma, can be used.

It has also been found that the plasminogen is not significantly activated into plasmin either at the time the contact phase is activated or during the operations involved in preparing the biological glue. Thus, contrary to what might be expected, there is no risk of the adhesion breaking prematurely due to fibrinolytic activity of the plasmin.

In the present application, the term "biological glue" designates an aqueous solution obtained by fractionation or concentration of blood plasma in order to concentrate the fibrinogen while preserving the necessary coagulation factors listed above, and possibly eliminating at least some of the other plasma proteins when it is undesirable to overload the biological glue with proteins such as albumin. Blood plasma contains 2 to 4 g/L of fibrinogen and 50 to 60 g/L of albumin. A biological glue obtained according to the invention can contain for example at least 10 g/L, and in particular at least 30 g/L of fibrinogen. Preferably, it contains less than 50 g/L of albumin, in particular less than 35 g/L, and in particular less than 30 g/L.

The biological glue obtained according to the invention can contain various added secondary ingredients such as viscosity enhancers or dyes for monitoring the application visually.

In the method according to the invention, obtaining the biological glue itself, i.e. obtaining a fibrinogen concentrate containing coagulation factors, is done by any known fractionation method, particularly by fractional precipitation according to known methods with the aid of a precipitator such as ethanol or polyethylene glycol. Of course, each candidate precipitator must be checked ahead of time to see that the necessary coagulation factors are present in the same fractions as the fibrinogen. For this purpose, in practice one need only check that the fibrinogen concentrate obtained is able to coagulate in less than 5 minutes merely by the addition of calcium ions, which requires only routine experiments.

Another known method comprises preparing a cryoprecipitate. For this purpose, the plasma is frozen, for example to a temperature less than or equal to −20° C., then the frozen product obtained is thawed, for example to a temperature of 0 to 5° C., in particular 2 to 4° C. This produces a plasma liquid and an insoluble product called cryoprecipitate which consists essentially of fibrinogen and various coagulation factors. This cryoprecipitate can be separated by centrifugation or by filtration; see for example document FR-2,718,033.

Another known method comprises concentrating the plasma using a membrane that allows water and low-molecular-weight components to pass through while holding back the proteins.

The invention also relates to a device for implementing the above-defined method in the case where the activator is an insoluble solid.

In one nonlimiting embodiment, this device is mainly characterized by containing a first container designed to receive the plasma before and/or during activation, a second container designed to receive the plasma after activation, means for transferring the plasma, in sterile fashion, from the first container to the second container, means for bringing about the contact between the plasma and a contact phase activator, and, if desired, means for separating the activated plasma from the activator so that the plasma collected in the second container is activator-free.

According to one particular embodiment, said contacting means comprise a tube in which the activator is confined, and said transfer means comprise tubing connecting an outlet orifice in the first container with one of the ends of the tube, and tubing connecting an inlet orifice of the second container to the other end of said tube such that the plasma is in contact with the activator in the tube when it circulates between the first container and the second container.

According to a second embodiment, the means for bringing about the contact between the plasma and the activator and separating the activated plasma from the activator comprise a compartment in which the activator is confined, said compartment being located inside the first container. The compartment has a liquid-permeable wall allowing contact with the activator as long as the plasma is in the first container, and also allowing separation of the plasma from the activator when the preactivated plasma passes into the second container.

In another embodiment, the means for bringing about the contact between the plasma and the activator comprise, inside the first container, a wall on which the activator is made to adhere by applying it as a coating for example, and in this case no means need be provided for separating the activated plasma from the activator.

The invention also relates to a method for using the biological glue as defined above. This method is characterized in that an aqueous solution containing calcium ions is added to said glue, without adding thrombin. The glue can then be applied in known fashion to the surgical area or the wound to be treated.

The calcium ions are added to the biological glue, in particular in the form of an aqueous solution, for example an aqueous calcium chloride solution. The quantity of calcium ions added is a sufficient quantity for the product obtained to contain "free" calcium ions, i.e. calcium ions not chelated by the complexing agent. This operation is called "recalcification." The quantity of free calcium ions must be a sufficient quantity to allow coagulation of the biological glue in a sufficiently short period of time. This quantity can be determined ahead of time by simple routine experiments.

BRIEF DESCRIPTION OF THE FIGURE

The FIGURE demonstrates the coagulation time of the cryoprecipitate of Example 5 as a function of the kallikrein content of the corresponding plasma after activation.

DETAILED DESCRIPTION OF PREFERRED EMBODIMENTS

Figure 1:
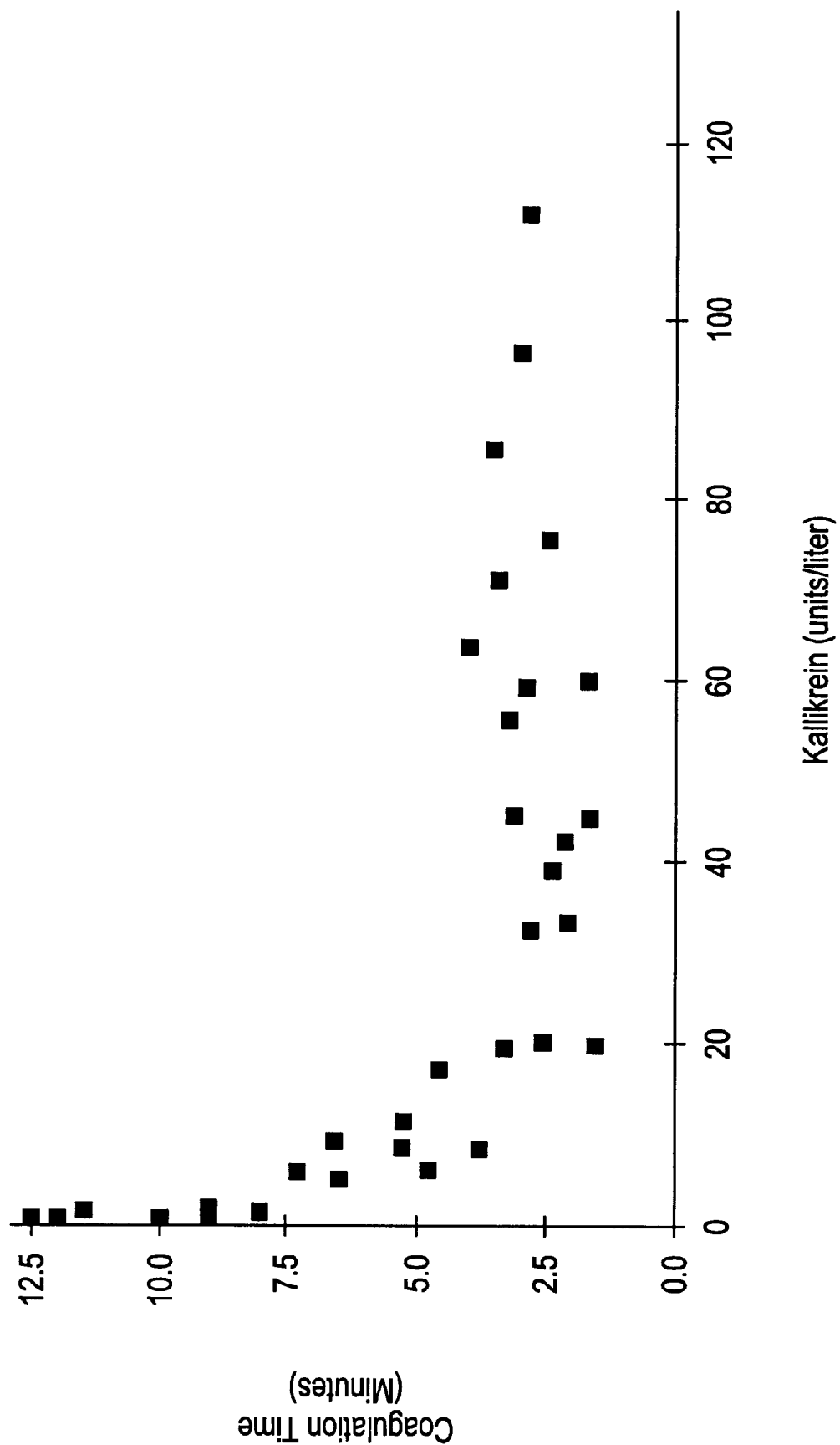

The following examples illustrate the invention.

EXAMPLE 1

The citrated blood plasma used as the starting product is a platelet-rich plasma obtained by centrifuging whole blood at 2000 G for 6 minutes. This plasma contains sodium citrate (170 mM).

2 cc of a 0.1 M zinc sulfate solution in 270 cc of said plasma cooled to 4° C. are added. The plasma is circulated in a polyvinyl chloride column containing 10 cc of coral granules with a particle size of 630–1000μ (Inoteb, St-Gonnery, France). The column dimensions are as follows: diameter: 1.4 cm; height: 14 cm.

The column is set up vertically, with its upper orifice connected via tubing to a pouch containing the blood plasma to which zinc sulfate has been added. Said pouch is located above the column and the plasma circulates by gravity flow. The lower end of the column has a filter for collecting the coral particles. This lower end is connected by tubing to a flexible pouch that collects the preactivated plasma.

The time taken for all the plasma to pass through the column is 45 minutes.

The kallikrein in the plasma is assayed as follows: 50 microliters of veronal-sodium acetate buffer with a pH of 7.35 (Diagnostic Stago, no. 360) is introduced into the well of a microtitration plate and either 50 microliters of a standard kallikrein solution (Chromogenix, Sweden, no. 820845) or 50 microliters of the sample to be assayed are added. The temperature is raised to 37° C. then 100 microliters of a 1.04 mM solution of substrate S-2302 (Chromogenix, no. 820340) preheated to 37° C. is added. The variation in optical density is measured at 405 nm for one minute and the kallikrein activity is deduced by comparing this variation in optical density with that observed for standard kallikrein.

The plasma kallikrein content after passage through the coral granules is 20 units per liter.

The plasma is then frozen to −30° C. then thawed for 24 hours in an enclosure at +4° C. The plasma obtained is centrifuged (2000 G). The centrifugation residue, i.e. the cryoprecipitate, is collected and heated to 37° C.

The time for the product (cryoprecipitate) obtained to coagulate is determined by thromboelastography using the "r+k" parameter; see for example S. V. Mallett and D. J. A. Cox, *British Journal of Anesthesia*, 69, 307–313 (1992). For this purpose, 175 μL of cryoprecipitate, temperature 37° C., is placed in the thromboelastography tank (Hellige). At 37° C., 175 μL of a 36 mM aqueous calcium chloride solution is added. The device automatically records the thromboelastography curve. The "r+k" parameter is measured from the curve. Since the paper on which the curve is plotted moves at a speed of 2 mm per minute, the coagulation time in minutes is equal to half the "r+k" length expressed in mm.

The coagulation time found is 2 minutes.

The cryoprecipitate can also be stored by freezing then thawed just before use.

A cryoprecipitate prepared as indicated above, namely freshly made or frozen then thawed, is stable for several hours at a temperature of 20° C.; spontaneous coagulation is not observed.

The cryoprecipitate obtained can also be stored by freeze-drying.

EXAMPLE 2

The procedure is as in Example 1 except for the fact that the coral granules are replaced by 14 g of is glass beads, diameter 200–300μ (Sigma, no. G.1277, L'Isle d'Abeau, France). The time taken for the plasma to pass through the glass bed column is 30 minutes. The plasma kallikrein content after passage through the glass beads is 19 units per liter.

The coagulation time of the cryoprecipitate, determined by thromboelastography, is 3 minutes.

EXAMPLE 3

The procedure is similar to Example 1, but the coral granules are replaced by kaolin powder (Sigma, no. K.7375). Various tests have been performed, using either a platelet-rich plasma (PRP) or a platelet-poor plasma (PPP) as the starting product.

The PRP and PPP plasmas were obtained as indicated below.

PRP is obtained by centrifuging drawn blood at 2200 G for 6 minutes.

PPP is obtained by centrifugation at 2500 G for 15 minutes.

For the cryoprecipitates obtained starting from PRP, the coagulation time is 100±30 seconds (mean of four tests).

For the cryoprecipitates obtained starting from PPP, the coagulation time is 190±35 seconds (mean of three tests).

EXAMPLE 4

The procedure is similar to that described in Example 1, on various samples of platelet-rich plasma.

The results are tabulated below.

TABLE I

| Sample No. | Kallikrein (units/liter) | Coagulation time (min) |
|---|---|---|
| 1 (a) | 2.9 | |
| (b) | 19.7 | |
| (c) | | 3.25 |
| 2 (a) | 3.6 | |
| (b) | 32.3 | |
| (c) | | 2.75 |
| 3 (a) | 4.5 | |
| (b) | 44.3 | |
| (c) | | 3 |

(a) starting plasma
(b) activated plasma (after passage through activator)
(c) cryoprecipitate In the following experiments (Samples 4 to 9), the number of platelets in the starting plasma was also 15 found, and the plasmin was assayed at various steps in the process. The results are summarized in Table II.

TABLE II

| Sample No. | Platelets (thousands per mm³) | Kallikrein (units/liter) | Plasmin* | Coagulation time (min) |
|---|---|---|---|---|
| 4 (a) | 37 | 3.1 | 0 | |
| (b) | | 67.7 | 0.33 | |
| (c) | | | 0.20 | 2.25 |
| 5 (a) | 368 | 7.1 | 0 | |
| (b) | | 67.5 | 0.35 | |
| (c) | | | 0.31 | 4 |
| 6 (a) | 23 | 3.3 | 0 | |
| (b) | | 34.8 | 0.20 | |
| (c) | | | 0 | 2.5 |
| 7 (a) | 33 | 5.5 | 0 | |
| (b) | | 29.8 | 0.41 | |
| (c) | | | 0.22 | 2.5 |
| 8 (a) | 421 | 7.9 | 0 | |
| (b) | | 97.6 | 0.42 | |
| (c) | | | 0.10 | 2.5 |
| 9 (a) | 261 | 5.6 | 0 | |
| (b) | | 29.8 | 0.20 | |
| (c) | | | 0.51 | 2.5 |

*% plasminogen converted into plasmin.

The meaning of (a), (b), and (c) is given after Table I above.

It can be seen that the plasminogen is not significantly activated into plasmin either at the time of activation of the contact system or during preparation of the cryoprecipitate.

Study of fibrinopeptide A release

It is known that fibrinogen is a dimer whose monomeric molecule has three chains, A$\alpha$, B$\beta$, and $\gamma$ (the total molecular weight of this monomer is approximately 170,000). Under the action of the thrombin, this molecule is partially hydrolyzed, releasing fibrinopeptide A (fp A) and fibrinopeptide B (fpB) at the rate of one fpA molecule and one fpB molecule per monomer molecule. The molecules that no longer contain fpA and fpB constitute the fibrin monomers that are associated with each other by hydrogen bonds and then form the soluble fibrin. The biological glue of the invention is practically fibrin-free, as shown by the fpA assay using for example the Asserachrom® (Stago) assay kit.

Fibrinogen content of biological glue: 50 g/l (mean of 5 preparations).

FpA content: 365 ng/ml (mean of 5 preparations).

The fpA content of the plasma is approximately 0 to 2.3 ng/ml and that of a standard platelet concentrate is approximately 14 ng/ml (Bode and Miller, *Vox Sanguinis* 51, 192–196, 1986).

Since the molecular weight of pfA is approximately 1500, it may readily be calculated that the proportion by weight of fibrinogen that has been hydrolyzed, releasing fpA, is approximately 0.08%. This proves that the biological glue of the invention is practically fibrin-free and hence practically thrombinfree.

EXAMPLE 5

The procedure is as in Example 1, varying the contact time with the activator and assaying the plasma kallikrein content each time after activation. It is found that the kallikrein content increases with activator contact time. A cryoprecipitate is then prepared with each plasma studied, then the coagulation times obtained after recalcification are measured. The results are summarized in the attached FIGURE, which represents the coagulation time of the cryoprecipitate as a function of the kallikrein content of the corresponding plasma after activation. It can be seen that the coagulation time is less than 5 minutes when the kallikrein content is at least equal to approximately 20 IU/L. More substantial activation (thanks to longer contact time with the activator) leads to increased plasma kallikrein content, but does not affect the coagulation time.

What is claimed is:

1. A method for preparing a biological glue, comprising fibrinogen and at least one coagulation factor, which, in aqueous solution, does not coagulate spontaneously for at least one hour at a temperature of 20° C., and which is able to coagulate in less than 5 minutes by adding calcium ions, comprising the steps of: a) obtaining blood plasma, and b) obtaining from said plasma a biological glue comprising fibrinogen and at least one coagulation factor, wherein, before and/or during step b), said plasma is placed in contact with a contact phase activator.

2. The method according to claim 1, further comprising subjecting the biological glue obtained in step b) to freeze-drying.

3. The method according to claim 1, wherein the plasma is placed in contact with the activator for a time sufficiently long to provide a plasma having a kallikrein content of at least 15 units per liter, said unit representing the quantity of kallikrein capable of hydrolyzing a 0.52 mM solution of D-prolyl-L-phenylalanyl-L-arginine-p-nitro-anilide in a veronal-sodium acetate buffer solution with a pH of 7.35, at 37° C., at the initial rate of 1 $\mu$mol/min.

4. The method according to claim 1, wherein said activator is an insoluble solid activator.

5. The method according to claim 4, wherein said solid activator is selected from the group consisting of kaolin, glass, Celite, calcium carbonate, coral, zinc oxide and zinc carbonate.

6. The method according to claim 4, wherein said activator contains a soluble activator insolubilized on a solid substrate.

7. The method according to claim 4, wherein the activator is separated and eliminated after the contact step.

8. The method according to claim 4, wherein the plasma is placed in contact with the activator in a container having a filter that allows the plasma to pass through while holding back the activator in order to separate the activated plasma from the activator after the contact step.

9. The method according to claim 4, wherein said contact is effected by circulating said plasma in a column containing the activator.

10. The method according to claim 9, wherein said plasma is circulated in the column up to an outlet orifice, said outlet orifice having a filter for holding back the activator.

11. The method according to claim 4, wherein the plasma and the activator are brought into contact in a container having an inside wall to which the activator is adhered.

12. The method according to claim 6, wherein said soluble activator is dextran sulfate or ellagic acid.

13. The method according to claim 1, wherein said activator is a soluble activator.

14. The method according to claim 13, wherein said soluble activator is dextran sulfate or ellagic acid.

15. The method according to claim 1, wherein the glue is a cryoprecipitate prepared during step b).

16. The method according to claim 1, wherein step b) is effected by fractional precipitation.

17. The method according to claim 16, wherein said fractional precipitation is carried out with the aid of a precipitating agent selected from the group consisting of ethanol and polyethylene glycol.

18. A device for implementing the method of claim 1, comprising: a first container designed to receive the plasma before and/or during activation, a second container designed to receive the plasma after activation, means for transferring, in a sterile fashion, the plasma from the first container to the second container, and means for bringing about the contact between the plasma and the contact phase activator.

19. The device according to claim 18, further comprising means for separating the activated plasma from the activator so that the plasma collected in the second container is activator-free.

20. The device according to claim 18, wherein said contacting means comprises a tube in which the activator is confined, and said transfer means comprises tubing connecting an outlet orifice in the first container with one end of the tube of the contacting means, and tubing connecting an inlet orifice in the second container to the other end of said tube of the contacting means, such that the plasma is in contact with the activator in the tube of the contacting means when the plasma circulates between the first container and the second container.

21. The device according to claim 18, wherein said contacting means comprise a wall inside the first container to which the activator is adhered.

22. The device according to claim 19, wherein said means for bringing about the contact between the plasma and the activator and said means for separating the activated plasma from the activator comprise a compartment in which the activator is confined, said compartment being located inside the first container and having a wall permeable to liquids.

23. A method for using the biological glue comprising fibrinogen and at least one coagulation factor obtained according to the method of claim 1, comprising adding an aqueous solution containing calcium ions to said glue, without adding thrombin, wherein in said method said fibrinogen is converted to fibrin.

24. The method according to claim 1, wherein said coagulation factor is an activated coagulation factor whose activation does not depend on calcium ions.

25. The method according to claim 24, wherein said coagulation factor is factor XIIa.

26. The method according to claim 25, wherein said coagulation factor is factor XIa.

27. The method according to claim 25, wherein said coagulation factor is factor VIIa.

28. The method according to claim 25, wherein said coagulation factor is factor kallikrein.

29. The method according to claim 23, wherein said coagulation factor is an activated coagulation factor whose activation does not depend on calcium ions.

* * * * *